United States Patent [19]

Gainer

[11] Patent Number: 5,093,494
[45] Date of Patent: Mar. 3, 1992

[54] FLAME RETARDANTS

[75] Inventor: James Gainer, Worsley, England

[73] Assignee: Ciba-Geigy Corporation, Ardsley, N.Y.

[21] Appl. No.: 415,009

[22] Filed: Sep. 29, 1989

[30] Foreign Application Priority Data

Oct. 6, 1988 [GB] United Kingdom ............. 8823482

[51] Int. Cl.$^5$ ..................... C07F 9/38; C07D 251/70
[52] U.S. Cl. .................................................. 544/195
[58] Field of Search ........................................ 544/195

[56] References Cited

U.S. PATENT DOCUMENTS

| | | | |
|---|---|---|---|
| 3,576,923 | 4/1971 | Randell et al. | 260/966 |
| 4,061,605 | 12/1977 | Simon | 260/45.8 |
| 4,241,145 | 12/1980 | Shukla | 428/537 |
| 4,260,688 | 4/1981 | Simon | 521/54 |
| 4,308,197 | 12/1981 | Byrd et al. | 428/272 |
| 4,452,849 | 6/1984 | Nachbur et al. | 428/264 |
| 4,487,800 | 12/1984 | Nachbur et al. | 428/265 |
| 4,623,642 | 11/1986 | Kristiansen et al. | 544/195 |
| 4,656,200 | 4/1987 | Clubley et al. | 521/108 |
| 4,950,757 | 8/1990 | Tomko et al. | 544/195 |

FOREIGN PATENT DOCUMENTS 286478 10/1988 European Pat. Off. .

OTHER PUBLICATIONS

Derwent Abstract of EPA 006,568, Jan. 9, 1980.
Chemical Abstract 89: 111478u (1978).

*Primary Examiner*—John M. Ford
*Attorney, Agent, or Firm*—JoAnn Villamizar

[57] ABSTRACT

The present invention provides a melamine phosphonic acid salt of the general formula (I)

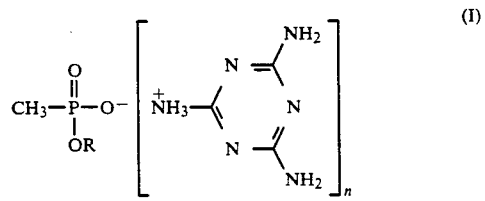

in which R is hydrogen, methyl or a negative valency bond, and n is 1 when R is hydrogen or methyl, or 2 when R$^1$ is a negative valency bond.

The salts are useful as flame retardants in polymers.

1 Claim, No Drawings

FLAME RETARDANTS

The present invention relates to melamine salts of phosphonic acids and their use in rendering polymers more flame retardant.

Polymers are often made more flame retardant by adding a phosphorus-containing compound, a halogen-containing compound or a mixture thereof. One commonly used phosphorus-containing compound is dimethyl methylphosphonate (DMMP). However there are certain problems associated with the use of DMMP, for example. it is a relatively volatile liquid (boiling point 181° C.) which means that material may be lost by volatilisation under certain circumstances.

Another flame retardant additive used, especially in high resilient polyurethane foams is melamine, but this needs to be used in comparatively large amounts to achieve a good effect.

We have now developed new melamine salts of methyl phosphonic acid which can be used and which avoid the disadvantages mentioned above.

Accordingly, the present invention provides melamine phosphonic acid salts of the general formula (I)

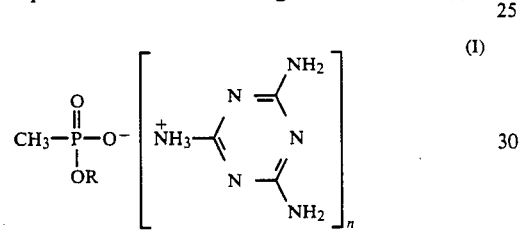

in which R is hydrogen, methyl or a negative valency bond, and n is 1 when R is hydrogen or methyl, or 2 when R is a negative valency bond.

The melamine salts may be prepared by reacting methyl phosphonic acid or its mono methyl ester with melamine in a suitable solvent such as water, an alcohol or mixtures thereof. The preferred solvent is water. The reaction may be carried out at temperatures from ambient up to the reflux temperature of the solvent.

The melamine salts may be used alone or together with other flame retardants such as those given below for imparting flame retardancy to various polymers.

Accordingly the present invention also provides a polymer containing a flame retardant amount of a melamine salt of formula (I) above.

The amount of melamine salt which may be incorporated in the polymer depends on the level of flame retardancy required. Typically the amount of melamine salt may be from 1 to 100 parts, preferably 3 to 50 parts by weight per hundred parts by weight of plastics.

Examples of polymers which may be rendered flame retardant are:

1. Polyurethanes and polyisocyanurates which are derived from polyethers, polyesters, or polybutadienes with terminal hydroxyl groups, and aliphatic or aromatic polyisocyanates, as well as precursors thereof (polyisocyanates, polyols or prepolymers) and including the so-called high resilence polyurethanes.
2. Polyphenylene oxides and sulfides, and blends of these polymers with polyamides, polyesters such as polybutylene terephthalate, polystyrene graft and copolymers such as high impact polystyrene, EPDM copolymers with rubbers.
3. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance, with polyethylene glycol, polypropylene glycol or polytetramethylene glycols.
4. Polyesters which are derived from dicarboxylic acids and dialcohols and/or from hydroxycarboxylic acids or the corresponding lactones, such as polyethylene terephthalate, polybutylene terephthalate, poly-1,4-dimethylol-cyclohexane terephthalate and polyhydroxybenzoates as well as block-copolyether-esters derived from polyethers having hydroxyl end groups.
5. Unsaturated polyester resins which are derived from copolyesters of saturated and unsaturated dicarboxylic acids with polyhydric alcohols and vinyl compounds as cross-linking agents of low inflammability.
6. Polystyrene.
7. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/ butadiene copolymes, as well as mixtures thereof with random copolymers of styrene of α-methylstyrene with dienes or acrylic derivatives, for instance the copolymer mixtures known as ABS-, MBS-, ASA-, or AES-copolymers.
8. Polycarbonates and blends thereof with other polymers such as ABS.
9. Crosslinked epoxide resins which are derived from polyepoxides, for example from bis-glycidyl ethers or from cycloaliphatic diepoxides.

The melamine salt may be used with other flame retardant compounds. These may be, for example, halogen-containing compounds such as aliphatic and aromatic bromine compounds, oxyalkylated phosphate esters, chloroalkyl phosphates, phosphonates or tri-aryl phosphates. Examples of suitable compounds are pentabromo-diphenyl ether, dibromocresvl glycidyl ether, tetrabromo bisphenol A, dibromoneopentyl glycol, a diol produced by the reaction of tetrabromophthalic anhydride with ethylene oxide and/or propylene oxide, tris (chloroethyl) phosphate, tris (monochloropropyl) phosphate, diethyl bis (hydroxyethyl) aminomethyl phosphonate, and isopropylated or t-butylated phenyl phosphate mixtures as described in British Patent Specification No. 1146173, tricresyl phosphate, trixylyl phosphate and cresyl diphenyl phosphate. The weight ratio of melamine salt to other flame retardant compounds may be from 5:95 to 95:5.

In the case of polyurethane foams, the melamine salts may also be used in conjunction with melamine itself, other melamine salts e.g. melamine borate or melamine phosphate, or exfoliated graphite as used in combustion modified foams.

The compositions of the invention may also contain other conventional ingredients, such as heat stabilisers, light stabilisers, ultra-violet light absorbers, anti-oxidants, anti-static agents, preservatives, adhesion promotors, fillers, pigments, lubricants, blowing agents, fungicides, plasticisers, processing aids, anti-dripping agents, impact strength modifiers and/or smoke suppressants.

The invention is illustrated by the following Examples in which "parts" are parts by weight.

EXAMPLE 1

A solution of methylphosphonic acid (28.8 parts, 0.3 mol) in water (50 milliliters) is added dropwise to a suspension of melamine (37.8 parts, 0.3 mol) in water (500 milliliters) at refluxing temperatures over 30 mins. A clear solution is formed. Heating is continued for a further 2 hours and the reaction mixture is evaporated to dryness under reduced pressure. The solid product is collected, washed with methanol and dried at 80° C. under vacuum to give 64 parts of methylphosphonic acid melamine salt having melting point >250° C. Calculated for $C_4H_{11}N_6O_3P$: %C 21.62, %H 4.95, %N 37.84, %P 13.96. Found: %C 21.51, %H 4.80, %N 37.64, %P 13.66.

EXAMPLE 2

Using the procedure described in Example 1, reaction of methylphosphonic acid (28.8 parts, 0.3 mol) with melamine (75.6 parts, 0.6 mol) gives 91 parts of the corresponding di-melamine salt having melting point >240° C. $^{31}P$ NMR ($H_2O$):=25.8 ppm.

EXAMPLE 3

Using the procedure described in Example 1, reaction of monomethyl methylphosphonic acid ester (94.5 parts, 0.75 mol) with melamine (82.5 parts, 0.75 mol) gives 163 parts of monomethyl methylphosphonic acid ester melamine salt having melting point >230° C. Calculated for $C_5H_{13}N_6O_3P1/2\ H_2O$: %C 24.51, %H 5.71, %N 34.30, %P 12.65. Found: %C 24.10, %H 5.65, %N 34.69, %P 12.35.

EXAMPLE 4

This example illustrates the ease with which flame retardant rigid foamed polyurethane compositions may be produced from polyols and polymeric diphenyl methane diisocyanate (MDI) in accordance with the present invention.

The following foam formulation is utilized to show the effect of flame retardant.

| Reactant | Concentration (parts) |
|---|---|
| Thanol ® R650x[1] | 100 |
| Water | 0.2 |
| Silcone surfactant | 2 |
| Trichlor fluoro methane | 40 (to foam density 30 ± 1 kg/m³) |
| Melamine salt | 10 |
| MDI | 117.5 |

[1] An aromatic polyol, viz. polypropoxylated (2-3 moles) (nonyl) phenol-diethanolamine-formaldehyde Mannich product (Texaco Chem.).

The above ingredients are mixed together for 10 seconds in a high speed stirrer (2000 rpm) at room temperature, with the isocyanate being added last, and then poured immediately into a cardboard mould. The exothermic reaction which ensues is allowed to free rise the foam.

Test specimens are cut from the foam after 3 days storage and subjected to the Limiting Oxygen Index Test (OI) and the BS 4735 horizontal Burn test. Results are shown in the Table below, and as a comparison the same foam material is produced without flame retardant.

TABLE 1

| Example | Salt from Example | Density kg/m³ | OI (%) | BS 4735 Burn Length mm |
|---|---|---|---|---|
| — | None | 30.0 | 21.3 | >150 |
| 4 | 1 | 27.0 | 23.3 | 26 |

EXAMPLE 5

This example illustrates the ease with which flame retardant flexible foamed polyurethane compositions may be produced from polyols and toluene diisocyanate in accordance with the present invention.

The following foam formulation was utilized to show the effect of flame retardant.

| Reactant | Concentration (parts) |
|---|---|
| Caradol ® 48/2[1] (a polyether polyol) | 100 |
| Silicone surfactant | 1 |
| Water | 4.7 |
| N,N-dimethylamino ethanol | 0.4 |
| Stannous octoate | 0.25 |
| Melamine salt | 10 |
| Toluene diisocyanate | 55.5 |

[1] Caradol is a polyether polyol (Shell).

The above ingredients are mixed together in a high speed hand held stirrer (2000 rpm) at room temperature for 10 seconds and then poured as quickly as possible into a cardboard mould. The exothermic reaction which ensues is allowed to free-rise the foam.

For comparison a foam is prepared from the same reactants without flame retardant.

Test specimens are cut from the foam after 3 days storage and subjected to the Limiting Oxygen Index Test (OI) and the BS 4735 horizontal burn test. The results are shown in Table 2 below.

TABLE 2

| Example | Salt from Example | Density kg/m³ | OI (%) | BS 4735 Burn Length mm |
|---|---|---|---|---|
| — | None | 19.8 | 16.8 | >150 |
| 5 | 3 | 30.8 | 23.6 | 70 |

EXAMPLE 6

Compositions are made up by melt compounding at a temperature of 230° C. 100 parts of the plastics based on polystyrene and polyphenylene oxide sold under the Trade Name (Noryl ®)731 (General Electric) and 12 parts of the salt from Example 1. A second sample was made containing no salt. Specimens were subjected to the Limiting Oxygen Index Test (OI) and also according to the "Test for Flammability of Plastics Material—UL 94", Feb. 1, 1984.

The UL 94 test is a well known test for the flammability of plastics. A strip of plastic material is held horizontally and a flame applied for a certain period of time to one end. If the strip burns, it has a rating HB i.e. horizontal burn. If it does not burn, another strip is held vertically over the flame which is applied for a certain time, depending on the extent of burning, whether there are any drips, self-extinguishing etc. There are three ratings given:- V-2, V-1 and V-0, where V-0 is the best. The results are shown below in Table 3.

TABLE 3

| Example | OI (%) | UL 94 |
|---|---|---|
| — | 19.5 | HB |
| 6 | 23.4 | V-1 |

EXAMPLE 7 AND 8

Compositions are made up by melt compounding at a temperature of 270° C. 100 parts of polybutylene terephthalate and 12 parts of the salt indicated in Table 4 below. The OI and UL 94 tests are carried out as in Example 6.

TABLE 4

| Example | Salt from Example | OI (%) | UL 94 |
|---|---|---|---|
| — | — | 19.1 | HB |
| 7 | 1 | 24.0 | V-2 |
| 8 | 3 | 22.9 | V-2 |

EXAMPLES 9 and 10

Compositions are made up by melt compounding at a temperature of 270° C. 100 parts of Nylon 6 ® and 12 parts of the salt indicated in Table 5 below. The OI and UL 94 tests are carried out as in Example 6.

TABLE 5

| Example | Salt from Example | OI (%) | UL 94 |
|---|---|---|---|
| — | — | 21.3 | HB |
| 9 | 1 | 25.1 | V-2 |

TABLE 5-continued

| Example | Salt from Example | OI (%) | UL 94 |
|---|---|---|---|
| 10 | 3 | 24.5 | V-2 |

EXAMPLES 11 AND 12

100 Parts of diglycidyl ether of bisphenol A (with epoxy content of 5.3 equivalents/kg) is mixed at 25° C. with 22 parts of TMD (equal parts of 2,2,4-trimethyl hexamethylenediamine and 2,4,4-trimethylhemamethylene diamine) together with 40 parts of the salt indicated in Table 6 below. The reaction mixture is gasses at 25° C., poured into a casting mould, allowed to stand for 18 hours at 25° C. and is finally heated at 100° C. for 1 hour. The end product is an opaque solid. The OI and UL 94 tests are carried out as in Example 6.

TABLE 6

| Example | Salt from Example | OI (%) | UL 94 |
|---|---|---|---|
| — | — | — | HB |
| 11 | 1 | 26.6 | V-0 |
| 12 | 3 | 27.5 | V-0 |

I claim:
1. A melamine phosphonic acid salt of the general formula (I)

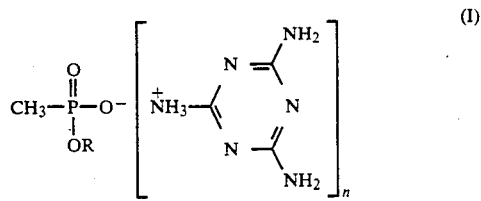

in which R is hydrogen, methyl or a negative valency bond, and n is 1 when R is hydrogen or methyl, or 2 when $R^1$ is a negative valency bond.

* * * * *